US009216283B2

(12) United States Patent
Ollivier et al.

(10) Patent No.: US 9,216,283 B2
(45) Date of Patent: Dec. 22, 2015

(54) MULTI-AREA PACING LEAD FOR A LEFT CAVITY OF THE HEART, IMPLANTABLE IN THE CORONARY NETWORK

(75) Inventors: Jean Francois Ollivier, Villiers le Bacle (FR); Frederic Anselme, Bois-Guillaume (FR); Nicolas Shan, Juvisy-sur-Orge (FR)

(73) Assignee: SORIN CRM S.A.S., Clamart (FR)

( * ) Notice: Subject to any disclaimer, the term of this patent is extended or adjusted under 35 U.S.C. 154(b) by 251 days.

(21) Appl. No.: 13/588,502

(22) Filed: Aug. 17, 2012

(65) Prior Publication Data
US 2013/0046370 A1  Feb. 21, 2013

(30) Foreign Application Priority Data
Aug. 18, 2011 (FR) .................................... 11 57394

(51) Int. Cl.
*A61N 1/05* (2006.01)
(52) U.S. Cl.
CPC ......... *A61N 1/056* (2013.01); *A61N 2001/0585* (2013.01)
(58) Field of Classification Search
CPC ..................................... A61N 1/056
USPC ................................. 607/122–126
See application file for complete search history.

(56) References Cited

U.S. PATENT DOCUMENTS

| 5,423,772 | A * | 6/1995 | Lurie et al. ............ 604/525 |
| 5,925,073 | A | 7/1999 | Chastain et al. |
| 6,178,355 | B1 | 1/2001 | Williams et al. |
| 6,385,492 | B1 | 5/2002 | Ollivier et al. |
| 6,556,873 | B1 * | 4/2003 | Smits ............ 607/122 |
| 2003/0208220 | A1 | 11/2003 | Worley et al. |
| 2003/0220677 | A1 * | 11/2003 | Doan et al. ............ 607/122 |
| 2004/0064024 | A1 | 4/2004 | Sommer |
| 2008/0177343 | A1 | 7/2008 | Dal Molin et al. |
| 2009/0157136 | A1 | 6/2009 | Yang et al. |

(Continued)

FOREIGN PATENT DOCUMENTS

| EP | 0993840 A1 | 4/2000 |
| EP | 1938861 A1 | 7/2008 |
| EP | 20100059847 | 5/2012 |

(Continued)

OTHER PUBLICATIONS

Foreign Search report (Annexe Au Rapport De Recherche Preliminaire Relatif A La Demande De Brevet Francais No. FR 1157394 FA 753635), Feb. 29, 2012.

*Primary Examiner* — Christopher D Koharski
*Assistant Examiner* — Michael D Abreu
(74) *Attorney, Agent, or Firm* — Foley & Lardner LLP

(57) ABSTRACT

A multi-area pacing lead implantable in a target vein of the coronary network for stimulating a left cavity of the heart, comprising an electrically conductive microcable (12), an electrically insulating outer coating, and carrying at its distal end a free active portion containing a plurality of separate denuded areas forming a network of active stimulation electrodes (14, 16), intended to contact the wall of target veins. The active free portion has a proximal corrugated portion carrying a first set of electrodes (14), a distal corrugated portion carrying a second series of electrodes (16) and an intermediate portion (20) that traverses an anastomosis (22) connecting the ends of two veins (VA, VPL). Both sets of electrodes (14, 16) can thus be placed in two different veins, defining two remote stimulation areas.

11 Claims, 2 Drawing Sheets

(56) References Cited

U.S. PATENT DOCUMENTS

2009/0299447 A1 12/2009 Jensen et al.
2012/0136423 A1 5/2012 Ollivier

FOREIGN PATENT DOCUMENTS

FR 2801509 A1 6/2001
WO WO 2006/023930 A2 3/2006

* cited by examiner

MULTI-AREA PACING LEAD FOR A LEFT CAVITY OF THE HEART, IMPLANTABLE IN THE CORONARY NETWORK

RELATED APPLICATION

The present application claims the priority date benefit of French Patent Application No. 11/57394 entitled "Multi-Area Pacing Lead For A Left Cavity Of The Heart, Implantable in The Coronary Network" and filed Aug. 18, 2011.

FIELD OF THE INVENTION

The present invention relates to active implantable medical devices as defined by the Jun. 20, 1990 directive 90/395/CEE of the European Community Council, including those devices that continuously monitor the cardiac rhythm of a patient and deliver, if and as necessary, to the heart electrical pulses for cardiac stimulation, cardiac resynchronization, cardioversion and/or defibrillation, and more particularly to cardiac pacing leads to be implanted in the coronary network of the heart to allow stimulation of a left or right heart cavity (ventricle or atrium). The present invention also relates to neurostimulation devices.

BACKGROUND

Unlike the right heart cavities, for which it is generally sufficient to implant endocardial leads via the right peripheral venous network, the implantation of permanent leads into a left heart cavity involves substantial surgical risks, in particular the risk of bubbles passing to the cerebral vasculature located downstream of the left ventricle.

One known technique, described for example by the U.S. Pat. Publication No. 2009/0299447 A1, is to apply an epicardial lead electrode against the outer wall of the myocardium, facing the cavity to be stimulated. But to stimulate a left heart cavity, instead of introducing a lead into the cavity directly, the technique that is most often used—and the one that is referred to by the present invention—is to introduce a lead into the coronary network. That lead is provided with an electrode that is to be applied against the wall of the epicardium, and oriented toward the left ventricle or the left atrium, as appropriate. These leads stimulate the heart muscle via one or more electrodes whose positions depends on the pre-defined trajectory of the cannulated vein.

A lead of this type is, for example, the SITUS LV (trademark) model, available from Sorin CRM (Clamart, France) and described in EP 0993840 A1 and its counterpart U.S. Pat. No. 6,385,492 (both assigned to Sorin CRM S.A.S., previously known as ELA Medical). Also, U.S. Publication No. 200310220677 A1 discloses a lead of the same type.

Such a lead is introduced into the coronary sinus from its opening in the right atrium. The lead is then pushed and oriented along the network of the coronary veins to the selected site. This procedure is very delicate, given the peculiarities of the venous system and its access paths, requiring passage through valves and tortuosities as well as the gradual reduction of the venous diameter as the lead progresses in the selected coronary vein.

Once the target vein is reached, the surgeon looks for a satisfactory pacing site, with good electrical contact of the stimulating electrode against the tissue of the epicardium, this contact having to be maintained despite the various variations or stresses over time.

It has been proposed to have multiple electrodes along the lead body and optionally to give the lead body a particular configuration to increase the chances of an acceptable compromise. [The surgeon can thus select, among the various electrodes present on the lead body, the one(s) providing the best efficiency from both the electrical and hemodynamic points of view. Such a multi-electrode lead is described, for example, in EP 1938861 A1 and its counterpart U.S. Pat. Publication No. 2008/0177343 (both assigned to Sorin CRM S.A.S., previously known as ELA Medical). These leads allow the implementation of a concept known as "electronic repositioning," aimed at directing or redirecting the electric field between different electrodes arranged along the pacing lead of the left ventricle and/or with one of the electrodes of the pacing lead of the right ventricle. This technology allows the management of micro-movements or changes in the hemodynamic behaviour (e.g., reverse modeling), simply by reprogramming the generator via telemetry through the patient's skin, without requiring any significant surgical intervention.

An alternative to this solution is an increasing complexity of the structure of the lead. For example, increasing the number of electrodes causes an increase in the number of components, and therefore of electrical connections. Or it requires the use of multiplexing circuits for the selection of the various electrodes present on the lead. However, these alternatives result in an increased risk of mechanical failure.

U.S. Pat. Publication No. 2009/157136 A1 describes a technique for finding an optimal pacing site using a temporary mapping catheter to be introduced into the coronary sinus. This catheter is either a flexible tube open at both ends, or a guidewire. In either case, it includes multiple electrically independent distal electrodes, and in the proximal portion a connector for connecting to an acquisition system for identification of the best stimulation site using an algorithm based on the cardiac motion. A classic permanent definitive multi-electrode lead of standard diameter from 4.5 to 6 French (1.5 to 2 mm) is then placed in the selected position, by use of an over the wire (OTW) technique in the case a guide wire is used, or through a lumen of a temporary introducer catheter if one is used.

Another recent development in the field of pacing the left ventricle is the reduction of the diameter of the portion implanted in the coronary network, to about a diameter of 4 French (1.33 mm). The size of the lead body is a factor directly related to the ability to control and guide the lead into and through the coronary venous system, in order to be able to select specific stimulation sites located in certain collateral veins. These sites are typically reached by use of a vein sub-selection catheter for the introduction of a guiding stylet to the chosen site. Once the vein is selected and stylet is introduced, the surgeon then advances the lead body by sliding it over the stylet, the latter acting as a support guide wire of small diameter, axially guiding the lead body until it reaches the selected location (i.e., the OTW technique).

These foregoing options, however, have recognized the existence of two competing limitations, which are:

The thinness of the lead, whose diameter determines whether or not allow it can reach the deepest collateral veins: thus, for the aforementioned SITUS LV lead, the lead has a diameter of 6.6 French (2.2 mm) and requires an introducer of 7 French (2.33 mm) in diameter, and The correct positioning and maintaining the good electrical contact of the electrode against the tissue for stimulation of wall of the epicardium.

The solutions proposed so far have been a compromise between these two constraints. For example, whereas the above techniques of using a multi-electrode lead or electronics repositioning allows, more or less, to overcome the second limitation, they exacerbate the first limitation because the multiplication of electrodes or internal conductors and components necessarily implies an increase in the diameter of the lead body and a reduction in its flexibility, making it difficult or impossible to pass through the tortuosities.

The present invention aims to overcome these two limitations, by providing a pacing lead for the left ventricle (and alternatively for the atrium) whose active part:

Has a very small diameter, to exploit the full length of the vein and to make optimal use of all the veins present in the basal zone;

Ensures excellent electrical contact with the tissues to be stimulated; and

Importantly, increases or expands the areas of stimulation, simultaneously allowing (unlike traditional leads) to stimulate several areas in the epicardium, thereby improving the chances of an optimal cardial resynchronization therapy (CRT).

In regard of the latter point, it has been found that multiple stimulation points on the left ventricle are a factor to improve substantially the quality of CRT.

Current studies nevertheless show that it is very difficult to concurrently implant two leads in the coronary venous system. A known alternative is to equip a lead body with several electrodes, up to four electrodes in some models. However, these leads have a relatively large diameter of about 4 French (1.33 mm), due to the complexity of components and connections necessary for the selection of electrodes for electronic repositioning. Furthermore, the relative position of the selected pairs of electrodes is very limited, these pairs of electrodes also being necessarily positioned in the same coronary vein, usually the posterolateral vein.

OBJECT AND SUMMARY

It is therefore an object of the present invention to propose a new configuration of a pacing lead having a very small diameter, to be implanted in the coronary venous system, for improving the efficiency of stimulation, by: (i) an enlargement of the stimulated area with (ii) the ability to stimulate two separate areas via two distinct veins, while (iii) maintaining the simplicity associated with the implantation of a single lead.

The starting point of the present invention is the recognition of the very frequent presence (typically 60 to 80% of the patient population) of distal anastomosis in the coronary venous system, that is to say that at the end of certain veins is a passage to another vein, thus with the possibility of communication between two distinct veins via the anastomosis at their respective distal ends.

One aspect of the present invention is broadly directed to a lead comprising a microcable, comprising a flexible element having a diameter of at most 2 French (0.66 mm) and an outer coating of an electrical insulation material, except for a selected number of "denuded areas" (where the insulation material has been removed or does not cover the microcable) that expose the underlying microcable, the denuded areas thus forming stimulating electrodes that are electrically connected together. Such a lead can then be a single—microcable passing in a first vein (herein called the "go" vein) followed by an anastomosis and into a second vein (called the "return" vein).

The small diameter microcable permits cannulation of veins of very small diameter, which heretofor have not been accessible due to the larger diameters of the permanent coronary leads of the prior art.

In one embodiment, the selected number of electrodes (the denuded areas) are distributed on the microcable and grouped into two distinct sets, a first set of electrodes to define stimulation sites in the "go" vein, and the second set of electrodes to define stimulation sites in the "return" vein. These two sets of electrodes are separated by an isolated intermediate length in the region corresponding to the most distal part of the go vein, the region of the anastomosis, and the most distal part of the return vein.

The electrode configuration of the microcable thus allows, with a single lead, to simultaneously stimulate two relatively remote areas, located in two separate veins. The remoteness of these areas and the proliferation of stimulation sites in each area provide a particularly beneficial effect for the resynchronization of the heart function (CRT).

In one embodiment, the microcable may be provided with a pre-shaped configuration to promote the electrode contact with the walls of the veins, and thus the electrical performance.

Advantageously, the microcable may, as discussed below, be made and implanted by conventional techniques well known to practitioners, thus not requiring any additional learning or technical skill.

In a preferred embodiment, the microcable of the present invention is used to cannulate the go vein according to a conventional method, by introducing a guide wire along the go vein, through the anastomosis and the return vein. A microcatheter is then advanced over the guide wire to the end thereof. The guide wire is then removed and replaced with the microcable carrying the two areas with their respective sets of stimulating electrode. Once the microcable is advanced through the lumen of the microcatheter (here, acting as an introducer) to its final position, the microcatheter is then retracted at least partially, sufficient to expose the two sets of electrodes providing two stimulating areas of the microcable, each being active in one of the respective go and return veins. The microcatheter also may be retracted entirely, where its continued presence is not longer required.

In one preferred embodiment, the present invention provides a novel pacing lead for implantation in a vein of the coronary network for the stimulation of a left ventricle of the heart. This lead comprises, as disclosed in the prior art, particularly from the U.S. Pat. Publication No. 2003/0220677 A1 cited above, a flexible element made of an electrically conductive material having at its distal end an active free portion comprising a plurality of denuded areas, intended to come into contact with the wall of a target vein of the coronary system, so as to form a network of stimulation electrodes electrically connected together. The flexible element further comprises, at its proximal side a connector plug that couples to a generator of an active implantable medical device, e.g., a cardiac pacemaker or a cardiac resynchronizer. The active free portion of the flexible element preferably comprises, at least, a proximal corrugated portion and a distal corrugated portion separated by an intermediate portion. The proximal and distal corrugated portions are elastically deformable between a free state, wherein the corrugation has an unstressed configuration, and a deployed state, wherein the corrugation is subject to radial stress as may be imposed by the target vein(s) in which the flexible element is introduced.

In a preferred embodiment, the flexible element is devoid of an internal lumen and has an outer diameter that is less than or equal to about 2 French (0.66 mm), the length in the axial direction of each of the corrugated portions is between about 1 and 5 cm in the deployed state, and the length in the axial direction of the intermediate portion is between about 5 and 20 cm.

In one embodiment, the overall dimension in the radial direction of each of the corrugated portions is between 10 and 25 mm in the free state.

In one embodiment, each of the corrugated portions present in the free state has form of a sinusoid with a denuded area at the top of each half period of the sinusoid and a denuded area at the end located at the distal side of the sinusoid.

In one embodiment, the total exposed surface of the denuded areas of the active free portion of the microcable is at most 10 mm.

In one embodiment, the microcable is formed of a plurality of microwire strands twisted or braided together. Preferably, at least some of the strands incorporate a core of radio-opaque material such as platinum-iridium or tantalum wrapped in a sheath of a mechanically durable material, such as NiTi or stainless steel, or vice versa:

In a preferred embodiment, the lead further comprises a hollow microcatheter made of a deformable material, and having a proximal end and a distal end and a central lumen open at its two ends, wherein the microcable is disposed to slide through and along the entire length of the microcatheter, such that in the deployed state the distal end of the microcable extends beyond the distal end of the hollow microcatheter, the distal part of the microcable emerging beyond the distal end of said microcatheter forming said active free portion. Preferably, the hollow microcatheter comprises at its distal end at least one bipolar stimulation electrode, not electrically connected to the microcable with the more distal bipolar stimulation electrode being distant from the most proximal denuded area of the microcable by an interval of between 5 and 15 mm. In one embodiment, the hollow microcatheter may comprise at its distal end at least one radiopaque marker for identification of the active free part of the microcable. The hollow microcatheter also may serve as an introducer catheter for implanting the microcable into the target vein(s).

Advantageously, the present invention proposes a lead that has a simple structure (and therefore is inexpensive to manufacture, and with maximum reliability) and which overcomes the described dual limitations associated with the design and use of multiple electrode leads, which, as described above, have a structural and functional complexity.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 1 generally illustrates the myocardium, with the main veins of the coronary system in which a lead in accordance with a preferred embodiment of the present invention, for stimulation of the left ventricle, is introduced;

DETAILED DESCRIPTION

Figure 1:
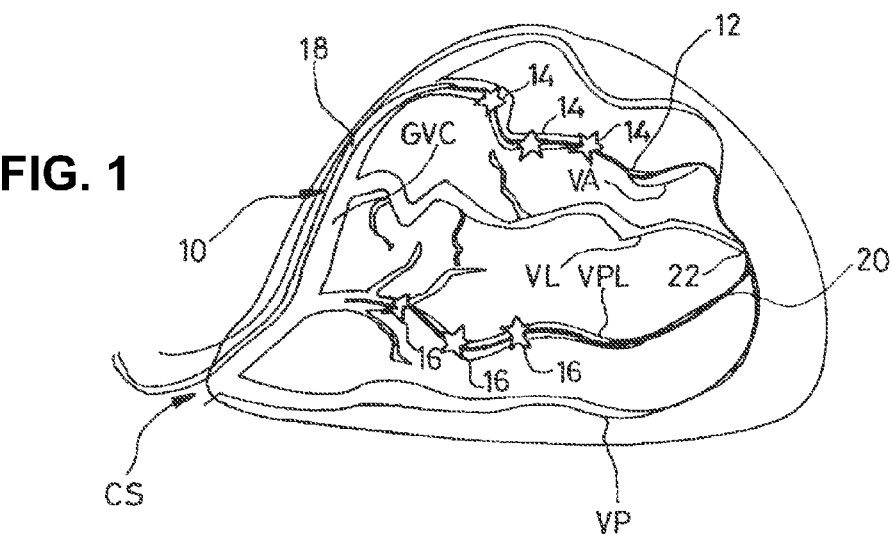

With reference to drawings FIGS. 1-5, examples of various embodiments of a lead in accordance with the present invention will now be described. FIG. 1 generally illustrates the myocardium and the major vessels of the coronary system, in which a lead of the present invention is introduced to stimulate the left ventricle. The reference 10 generally designates the lead according to the present invention.

Lead 10 is implanted in the intracardiac venous coronary system via the superior vena cava, the right atrium and the CS input of the coronary sinus vein. The coronary venous system then develops into several branches from the great cardiac vein ("GVC"), these branches including the posterolateral vein ("VPL"), the lateral vein ("VL"), the anterolateral vein ("VA") and the posterior vein ("VP").

Lead 10 preferably comprises a microcable 12 (whose distal portion is shown in isolation FIG. 2) introduced into anterolateral vein VA and which carries a first set of a plurality of stimulation electrodes 14 for stimulation of the left ventricle from multiple sites in vein VA. Lead 10 further comprises, in its proximal region, a microcatheter 18 shown with its distal portion entering the coronary sinus and great cardiac vein GVC to the outlet of anterolateral vein VA.

In a preferred embodiment, microcable 12 also includes, at a distance from electrodes 14, a second set of a plurality of electrodes 16 to stimulate the left ventricle from another vein, for example, the posterolateral vein VPL via a communication by an anastomosis 22 connecting the anterolateral vein VA and the posterolateral vein VPL. Microcable 12 crosses anastomosis 22 and the more distal regions of the two veins VA and VPL along an intermediate portion 20 that is preferably devoid of electrodes.

As a result of this configuration, it is possible not only to stimulate the left ventricle at several points along one of the veins (due to the increasing number of electrodes 14 or 16), but also to provide two relatively remote areas with stimulation, respectively the area of a first set of electrodes 14 and the area of a second set of electrodes 16, located in proximal regions of two different veins in which it would have been difficult to stabilize or fix conventional leads for stimulation of the left ventricle, because of the large diameter of the opening of these veins.

Microcable 12 has a diameter at most equal to 2 French (0.66 mm), typically on the order of 0.5 to 2 French (0.16 to 0.66 mm). Microcable 12 is advantageously made of a material whose main advantage is extreme durability and resistance to fatigue, for example, nitinol (NiTi alloy) or an MP35NLT steel. These materials also have the requisite corrosion resistance at the exposed electrodes.

Figure 5:
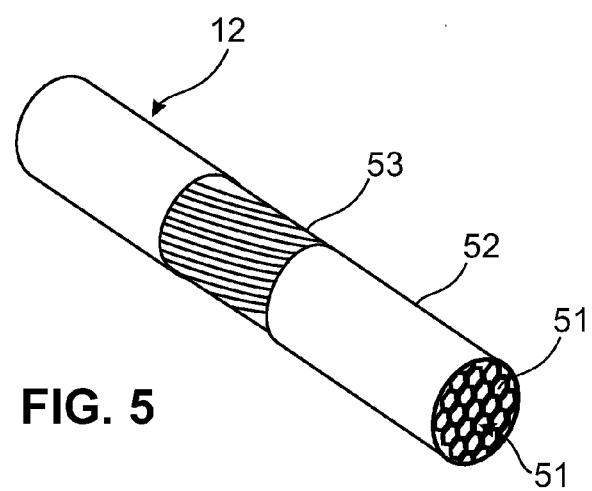
FIG. 5 illustrates an elevated perspective view of a section of a lead of FIG. 4b.

With reference to FIG. 5, In a preferred embodiment, the structure of microcable 12 comprises a cable made of multiple microwire strands 51 braided together where the microwire strands 51 are preferably a platinum-iridium core sheathed by a thickness of MP35NLT steel or nitinol—or vice versa—in order to optimize the response to the dual requirements of corrosion resistance and fatigue resistance.

The assembly can then be coated or covered with an insulating material 52. The thickness of the insulating layer that is required is a thickness sufficient to provide good electrical insulation, e.g., more than 0.1 mm, which is well understood by a person of ordinary skill in the art. In one embodiment, the coating may be formed by applying a thin layer of parylene (for example, of type C). In this embodiment, coating is denuded, i.e., more or less complex openings in the coating are made, at desired locations along microcable 12, for example, by plasma ablation. These denuded areas 53 form the electrically active areas (electrodes) 14 and 16. To improve electrical performance, these active areas 53 may be further coated, for example, with titanium nitride (not shown).

In an alternative embodiment, the coating may be formed by a polyurethane tube in which the denuded areas are formed by aperatures provided at the locations of the active areas 53 of electrodes 14 and 16, when the tube is placed over microcable 12. In this embodiment, the aperatures formed in the tube provide the denuded areas 53 that expose the underlying microwire strands 51.

In yet another alternative, the coating may be made of one or more layers made of tubes made of PET (polyethylene terephthalate), fluoropolymer, PMMA (polymethyl methacrylate), PEEK (polyetheretherketone), polyimide or other suitable similar material.

Such a microcable structure, without an internal lumen and with several microwires braided together, is capable of both endurance (against cardiac movements) and resistance to stresses related to implantation and corrosion.

These types of microcables and microwires are commercially available, for example, from Fort Wayne Metals Inc. Fort Wayne, Ind., USA, and are known for use in the medical field, in particular for producing defibrillation conductors— but in an arrangement of different materials: in these prior known applications the structure is a stranded structure in which each strand includes a core of silver (to improve conductivity) coated by a steel layer. These prior art microstructures, isolated or not, are then incorporated into a multi-lumen lead body of classic construction.

In an alternative embodiment in accordance with the present invention, microcable 12 may be comprised of the foregoing microwires braided around a platinum-iridium wire in the center of a 1×7-multi-microwire structure, the more fragile platinum-iridium strand then being embraced by the more durable outer strands.

In yet another embodiment, the platinum-iridium can be replaced by any radio-opaque material such as tantalum.

The denuded portions of the coating exposing electrodes 14 and 16 form a succession of individual electrodes, together constituting an array of electrodes, preferably configured as at least two sets of electrodes, connected in series for multiplying the points of contact with the wall of the vein(s). This ensures a multi-area transmission of the stimulation energy at several points of the coronary system and thus of the left ventricle.

The surface area of each individual electrode is preferably at most 1 mm$^2$, which allows providing a relatively large number of electrodes while not exceeding a cumulative total surface area of about 10 mm$^2$. The low cumulative surface area brings the associated benefits of a "high current density" lead, in terms of both physiological stimulation efficacy and lower energy consumption. This is achieved while maximizing the likelihood of physical, therefore electrical, contact of the electrodes 14, 16 with excitable tissues, due to the multiplication of these electrodes and to their position at the top of the corrugations.

Figure 2:
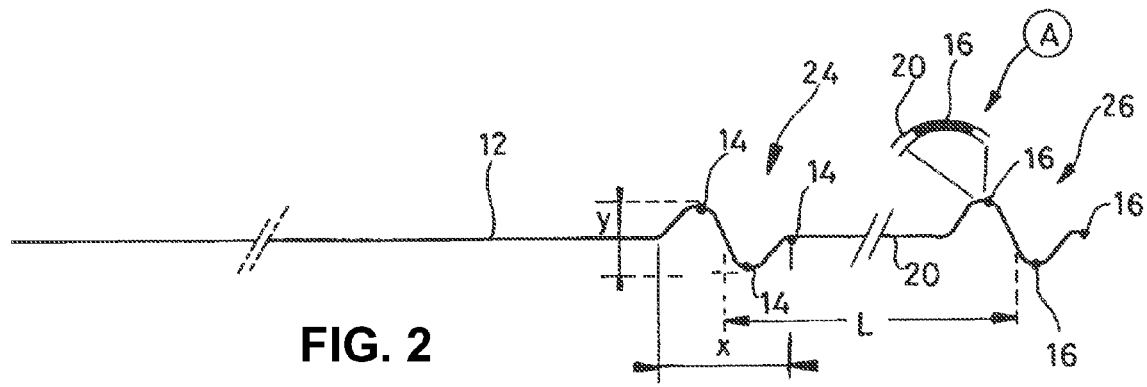
FIG. 2 illustrates the end portion of the lead of FIG. 1.

With reference to FIG. 2, a preferred configuration of the distal portion of microcable 12 is shown. Two corrugated portions 24, 26, for example, in the form of a period of a sinusoid are illustrated. These two corrugated portions 24, 26 correspond to the two respective areas of stimulation, namely, a first set of electrodes 14 in the antero-lateral vein VA, on the one hand, and a second set of electrodes 16 in the postero-lateral vein VPL, on the other hand.

Note however that, although in this example two corrugated portions are represented, it is possible to have a higher number, for example, if a stimulation of several areas of one and/or the other vein is desirable, instead of a single zone in each vein. Similarly, the illustrated example which shows three electrodes for each of the corrugated portions, and hence three points of stimulation in each zone, is in no way limiting, and it is possible to provide a smaller or larger number of electrodes in each these areas. It also should be understood that each set of electrodes need not have the same number of electrodes.

Preferably, the corrugation of each of the portions 24, 26 is a pre-shape given to the microcable in the free state, with, for example, a length x of the period of a sinusoid on the order of 30 mm, and a total amplitude y in the radial direction on the order of between about 10 and 25 mm. In the described example, which should be understood to be non-limiting, the two portions 24, 26 form two corrugations extending in a common plane. Alternatively, however, it is possible to construct a structure in which the corrugations of the portions 24, 26 extend in the three dimensions of space, each of corrugated portions 24, 26 typically extending in a cubic envelope of about 25 mm on a given side.

The two corrugated portions 24, 26 are separated by an intermediate portion 20 whose length L is preferably between about 5 and 15 cm.

In the described example, the electrically isolated intermediate portion 20 is represented as straight and not corrugated. Alternatively, it is possible to provide intermediate portion 20 with a corrugation or an appropriate pre-shape to locally promote the retention of microcable 12 through the reduced diameter of the anastomosis.

As a result of the elasticity of microcable 12, the pre-shapes of the corrugated portions 24, 26, are deformable under radial stress during passage through the veins of the coronary system, as illustrated in the configuration shown in FIG. 1. It should be understood that the pre-shapes provide a bias that promote contact of electrodes 14, 16 with the tissues, and thus their electrical performance.

Preferably, electrodes 14, 16 are located at the top of each half cycle of the sinusoid, as is more specifically shown on the detail illustration marked A in FIG. 2.

The simplicity of the structure—an isolated microcable, with occasionally denuded areas forming the electrodes—advantageously allows without difficulty a localization of an electrode at the top of the sinusoidal wave, which would be much more difficult to achieve with a conventional coronary lead structure. Indeed, these areas of maximum curvature are a priori the most stressed areas in operation, which generally leads the manufacturers of conventional leads to locate the electrodes halfway between the peaks, although these areas are significantly less favorable to make a good electrical contact with the wall of the vein.

In addition, this localization of the exposed portions of electrodes 14, 16 offers the possibility to sectorize the electrodes. In other words, to ensure that, viewed in cross section, the electrodes do not extend around the entire periphery of the microcable, but only on an angular sector located on the side of the outer face of the curvature, i.e., the surface facing the tissues with which the electrode is to contact and operate. It is thus possible to keep the inside of the curvature of microcable 12 isolated by the coating to minimize the stimulating electrode surface area, with the advantages outlined above.

In a preferred embodiment, an electrode 14, 16 is also located at the end of the period of the sinusoid, on the distal side. Indeed, in another embodiment, a fourth electrode, located at the proximal end of the period of the sinusoid, could also exist in each set of electrodes.

Figure 3:
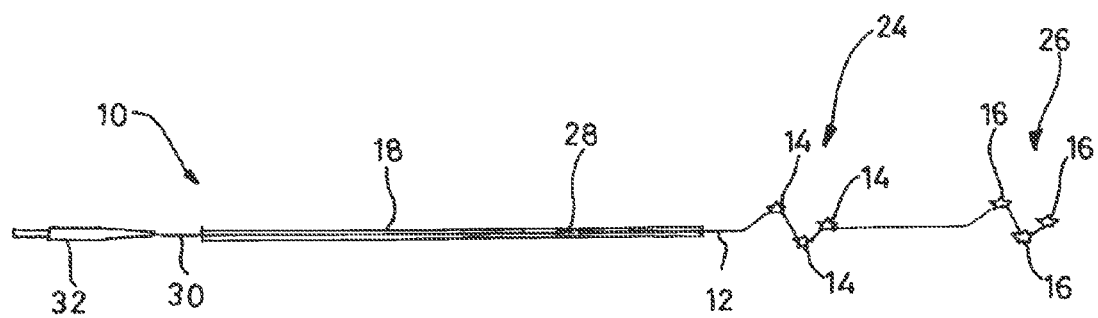
FIG. 3 illustrates all the elements of a lead in accordance with a second preferred embodiment of the present invention for unipolar pacing.

With reference to FIG. 3, all the elements of a lead are depicted, with microcable 12 housed in a microcatheter 18. The proximal portion 30 of microcable 12 is extended from a connector 32, which connector a prori is constructed in accordance with a suitable industry standard, e.g., standard IS-1, and is factory assembled.

One suitable technique for the implantation of a lead 10 according to the present invention will now be discussed. Initially, the surgeon uses a main catheter for accessing an opening of the coronary sinus, and a sub-selection catheter to choose, under fluoroscopy, the path of the venous system to access the target vein. Lead 10 is then preferably implanted by a conventional OTW technique using a very thin stylet forming a guide wire, provided at its distal end with a very flexible termination that is not traumatic and allows its direct introduction into the vessels of the coronary system without significant risk of perforation.

With respect to the tracking performance of the microcable, for example, its poor torque transmission and thrust from its proximal end, and its great flexibility, are characteristics that do not allow a direct cannulation of the "go" and "return" veins. Thus, it is necessary to first introduce a guide wire (not shown) and then microcatheter 18.

For this purpose, the surgeon inserts the guide wire into the sub-selection catheter, pushes it forward into the coronary venous system in order to select a particular collateral vein, in the present case the selected "go" vein (here, preferably, the anterolateral vein VA), then the anastomosis 22 and finally the selected "return" vein (here, preferably, the posterolateral vein VPL) and passing it into the latter.

The surgeon then puts microcatheter 18 on the guide wire, and slides it and advances it over and along the guide wire until reaching the end of the latter. The guide wire is then removed. After removal of the guide wire, microcable 12 is inserted inside the lumen of microcatheter 18 from the proximal end thereof, and pushed through the entire length of microcatheter 18. Microcatheter 18 is then removed at least far enough to expose corrugated portions 24 and 26 and thus electrodes 14, 16, i.e., the active free portion of microcable 12. (See e.g., FIGS. 1, 3, 4a, and 4b.) More particularly, this achieves the configuration represented in FIG. 1, with the two sets of electrodes 14 and 16 arranged at the respective chosen stimulation sites.

It will be understood by a person of ordinary skill in the art that these steps of vein cannulation are already widely practiced by specialists of this implantation technique, so that the implantation of a lead according to the present invention requires no new operating technique or additional specific skill.

It should be understood that the present invention allows an optimal placement of the microcable as a result of using the combination of a guide wire and microcatheter, and a simplicity and robustness of the assembly, despite the very small diameter of the components. Indeed, the electrical conduction line of the microcable contains no critical connection, such as welding or gluing, presenting a risk of mechanical failure, and instead the electrical conduction line consists of a unique and robust element, i.e., the microcable.

Figure 4A:
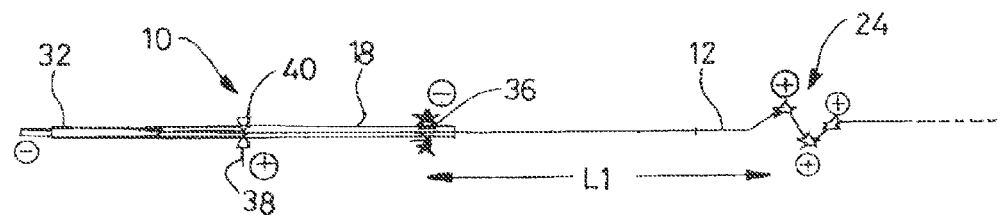
FIGS. 4a and 4b illustrate two variants of a lead according to the invention, in a third embodiment for bipolar pacing.
Figure 4B:
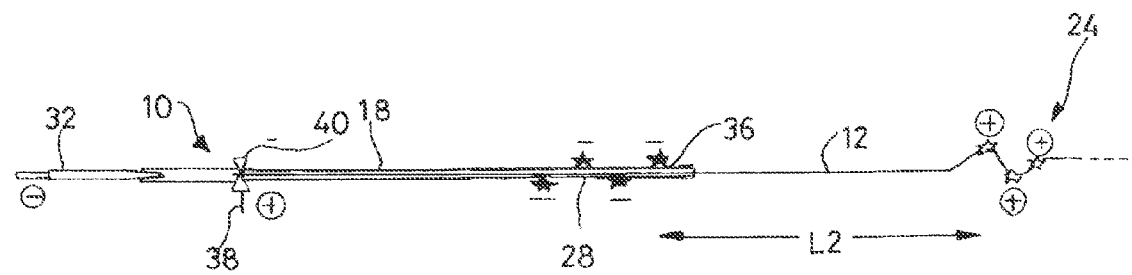

FIGS. 4a and 4b illustrate two variant embodiments of the present invention, in a configuration for bipolar pacing. In these figures, microcatheter 18 also carries electrodes 36, individually or collectively connected to a specific conductor 38, isolated from microcable 12.

This connection is achieved by means of a connection device 40 as described for example in French patent application 10 59 847 dated Nov. 29, 2010 and its counterpart U.S. Pat. Publication No. 2012/0136423 on behalf of the Applicant, for a "System for stimulation and/or defibrillation for the left ventricle endocardially or from a vein in the coronary system," which is incorporated herein by reference. This document describes a device for carrying out both an electrical contact on a microcable and a mechanical immobilization thereof with respect to a sheath, i.e., the microcathater in the context of the present invention, while ensuring the electrical continuity of another conductor extending along the sheath and connected to an electrode carried by the lead body.

The additional electrodes 36 may be arranged either on the main body of microcatheter 18 (FIG. 4a) or on the distal portion 34 thereof (FIG. 4b). In the first case, a minimum interval L1 is provided between electrodes 36 and electrodes 24 on the order of from 5 to 10 cm, and in the second case a minimum interval L2 of 15 is provided on the order of from 5 to 15 cm. These parameters are determined by partial withdrawal of the microcatheter With such a configuration, it is possible to produce a bipolar stimulation between, on the one hand, electrode 36, and on the other hand, electrodes 14 and 16. In the absence of electrode(s) 36, the stimulation is a monopolar stimulation between, on the one hand, the housing of the generator (not shown), and on the other hand, electrodes 14 and 16.

Another variation (not shown) for a bipolar configuration is to juxtapose two microcables that are immobilized and isolated in a common miniaturized multi-lumen sheath, both microcables being individually connected at both poles to the connector 32. It is thus possible to alternate the polarity of the electrodes in a same stimulation area (area of electrodes 14 or 16), by selectively removing the insulating sheath over a portion of the periphery. A quadripolar variation on the same principle is also possible.

One skilled in the art will appreciate that the present invention can be practiced by embodiments other than those described herein, which are provided for purposes of illustration and explanation, and not of limitation.

The invention claimed is:

1. A pacing lead, for implantation in a target vein of the coronary venous network for the stimulation of a left chamber of a patient's heart, comprising:
 a distal end, a proximal end, and a flexible element made of a conductive material;
 a coating of an electrically insulating material surrounding said flexible element, the distal end having a free active portion comprising a first set of a plurality of electrodes and a second set of a plurality of electrodes, each formed by a plurality of separate denuded areas of said coating, said electrodes forming a group of electrodes electrically connected together to each contact a wall of a target vein, the proximal end comprising a connector for coupling to a generator of an active implantable medical device wherein:
 the free active portion further comprises, a proximal corrugated portion and a distal corrugated portion separated by an intermediate portion, wherein the proximal corrugated and distal corrugated portions are elastically deformable between a free state in the absence of a radial stress and a deployed state in the presence of a radial stress, and wherein the corrugated portions are given a pre-shape by constructing the portion of the lead with a series of alternating bends in the free state;
 wherein the intermediate portion is non-corrugated and straight in the free state;
 wherein the proximal corrugated portion comprises the first set of a plurality of electrodes and the distal corrugated portion comprises the second set of a plurality of electrodes;
 the flexible element is free of any internal lumen and comprises a microcable having a diameter of less than or equal to 2 French (0.66 mm); and the length in the axial direction of each of the corrugated portions is between 1 and 5 cm in the deployed state, and the length in the axial direction of the intermediate portion is between 5 and 20 cm.

2. The lead of claim 1, wherein each of the corrugated portions has in the free state a shape in the form of a period of a sinusoid.

3. The lead of claim 2, wherein the plurality of electrodes includes a denuded area located on the top of each half period of the sinusoid.

4. The lead of claim 2, wherein the plurality of electrodes includes a denuded area on the distal side end of the period of the sinusoid.

5. The lead of claim 1, further comprising a hollow microcatheter made of a deformable material, having a proximal end and a distal end and a central lumen open at said proximal and distal ends, wherein the microcable can slide in the lumen over the entire length of the microcatheter and beyond the distal end thereof, wherein a part of the microcable emerges beyond the distal end of the microcatheter in the deployed state and comprises said free active portion.

6. The lead of claim 5, wherein the hollow microcatheter further comprises at least one distal bipolar stimulation electrode, not electrically connected to the microcable.

7. The lead of claim 6, wherein the most distal bipolar stimulation electrode of the hollow microcatheter is spaced from the most proximal electrode of the microcable by an interval of between 5 and 15 mm.

8. The lead of claim 1, wherein the microcable further comprises a plurality of microwire strands of which at least some of the plurality of microwire strands incorporate a core of a radio-opaque material wrapped in a sheath of a mechanically durable material or vice versa.

9. The lead of claim 8 wherein the mechanically durable material is a NiTi alloy or a stainless steel.

10. The lead of claim 1, wherein the overall dimension in the radial direction of each of the corrugated portions is between 10 and 25 mm in the free state.

11. The lead of claim 1, wherein the total denuded surface area of the plurality of electrodes of the free portion of the microcable is not more than 10 $mm^2$.

* * * * *